United States Patent [19]

Kuroya et al.

[11] Patent Number: 5,137,729
[45] Date of Patent: Aug. 11, 1992

[54] DRUG PREPARATION APPLICABLE TO ORAL MUCOSA

[75] Inventors: Takamasa Kuroya; Yuichi Inoue, Osaka, Japan

[73] Assignee: Nitto Denko Corporation, Osaka, Japan

[21] Appl. No.: 472,933

[22] Filed: Jan. 31, 1990

[30] Foreign Application Priority Data

Jan. 31, 1989 [JP] Japan ................................. 1-23305

[51] Int. Cl.⁵ ................... A61F 13/02; A61K 31/78; A61K 9/70; A61L 15/16
[52] U.S. Cl. ................... 424/435; 424/78.08; 424/78.31; 424/484; 424/486; 424/487; 424/488; 514/54; 514/57; 514/777; 514/778; 514/784; 514/785; 514/944; 514/945; 514/953; 514/955
[58] Field of Search ............ 424/81, 78, 443, 447, 424/448, 449, 484, 486, 487, 488, 435; 514/54, 57, 777, 778, 784, 785, 944, 945, 953, 955

[56] References Cited

U.S. PATENT DOCUMENTS 4,666,441  5/1987  Andriola et al. ..................... 424/448
4,921,695  5/1990  Babaian et al. ...................... 424/81

FOREIGN PATENT DOCUMENTS 0020777  1/1981  European Pat. Off. .
0106107  4/1984  European Pat. Off. .
0200508  12/1986  European Pat. Off. .
0241179  10/1987  European Pat. Off. .
0275550  7/1988  European Pat. Off. .

OTHER PUBLICATIONS

Chemical Abstracts, vol. 99, No. 22, Abstract No. 181420z, 1983.
Chemical Abstracts, vol. 83, Abstract No. 103302t, 1975.

*Primary Examiner*—Thurman K. Page
*Assistant Examiner*—Carlos Azpuru
*Attorney, Agent, or Firm*—Sughrue, Mion, Zinn, Macpeak & Seas

[57] ABSTRACT

A drug preparation applicable to the oral mucosa is disclosed, comprising a soft adhesive film containing a systemic drug, the adhesive film comprising a homogeneous mixture comprising a vinyl acetate homopolymer, an acrylic acid polymer, and a cellulose derivative capable of being dissolved in or swollen with water and a lower alcohol. The drug preparation is less causative of an adverse feeling in the oral cavity on use, excellent in shape retention on water absorption, and adhesive to the oral mucosa for an extended period of time, thereby achieving a stable administration of a systemic drug for a long time.

12 Claims, 2 Drawing Sheets

DRUG PREPARATION APPLICABLE TO ORAL MUCOSA

FIELD OF THE INVENTION

This invention relates to a drug preparation which is applied to the wet mucosa of the oral cavity to maintain a long-term administration of a systemic drug.

BACKGROUND OF THE INVENTION

Known dosage forms for intraoral administration of drugs include solutions, ointments, troches, buccal tablets, sublingual tablets, etc. Recently, slow-releasing intraoral tablets of track-field type which are less causative of a feeling of foreign matter (as described in JP-A-55-59109, JP-A-58-154547, and JP-A-58-154548, the term "JP-A" as used herein means an "unexamined published Japanese patent application") and slow-releasing Nifedipine tablets of track-field type applied to the oral mucosa (as described in JP-A-61-15829 and JP-A-61-17510) have been proposed. For the purpose of further reducing an adverse feeling in the oral cavity, medical bandage using, as a base, a water-soluble high polymer which exhibits adhesion when dissolved or gelled with water (as described in JP-A-60-142927), preparations applicable to the oral mucosa comprising a water-soluble film having incorporated thereinto a steroid or non-steroid agent (as described in JP-A-61-280423), and sheet preparations comprising a support sheet having thereon a drug, gelatin, agar, gluten, a carboxyvinyl polymer, a polyhydric alcohol, a gum, and a wax as essential components (as described in JP-A-61-85315) have also been proposed.

More recently, there have been proposed bases for application to the oral mucosa which comprise a mixture of a water-soluble substance and a water-insoluble substance; for example, intraoral bandage composed by a soft film in which at least one of a polycarboxylic acid and a polycarboxylic acid anhydride, and a vinyl acetate polymer are mixed in a compatible state as disclosed in JP-A-61-249472 and JP-A-61-249473; a base comprising a water-insoluble or sparingly water-soluble support having thereon an adhesive layer containing an acrylic acid polymer which exhibits adhesion when dissolved in or swollen with water and a water-insoluble cellulose derivative as disclosed in JP-A-63-160649; a composite for application to the oral mucosa comprising a surface layer containing ethyl cellulose and a vinylpyrrolidone polymer or copolymer having thereon an adhesive layer as disclosed in JP-A-63-171564 and JP-A-63-171565; and an adhesive composition containing a vinylpyrrolidone polymer or copolymer, at least one of hydroxyethyl cellulose and hydroxypropyl cellulose, and a water-retaining softener as disclosed in JP-A-63-174660.

However, none of these known intraoral preparations or bases satisfies both duration of adhesion and freedom from an adverse feeling in the oral cavity on use. For example, since solutions, ointments or the like preparations easily run away with saliva or other water content, it is difficult to maintain efficacy for a long time with these preparations. Troches, which are large tablets prepared by punching a mixture of a drug and a base, e.g., saccharides, cause a considerable adverse feeling. Buccal tablets and sublingual tablets are generally designed for rapid mucosal absorption of drugs and are, therefore, of short duration. The track-field type tablets, though slowly releasing a drug, have a thickness as large as 1.3 to 3 mm and lack softness, still involving the problem of an adverse feeling on use. The preparations for application to the oral mucosa comprising a water-soluble film containing a drug have softness and thereby cause a reduced adverse feeling in the oral cavity. However, since the film base is water-soluble, it is easily dissolved in saliva or water contents in the oral cavity and is, therefore, poor in duration of efficacy. The bases comprising a mixture of a water-soluble substance and a water-insoluble substance are soft and less causative of an adverse feeling upon use. Also, they take time to disappear in the oral cavity and are thus expected to have a longer duration of pharmaceutical effects as compared with bases comprising a water-soluble substance alone. These bases nevertheless exhibit adhesion only for 2 to 10 hours at the longest.

Hence, an intraoral preparation satisfying all the three requirements, i.e., freedom from a feeling of foreign matter on use, excellent shape retention on water absorption, and long-term adhesion to the wet oral mucosa, has not yet been developed.

SUMMARY OF THE INVENTION

An object of this invention is to provide a drug preparation applicable to the oral mucosa for administering a systemic drug, which is less causative of an adverse feeling in the oral cavity on use, excellent in shape retention on water absorption, and adhesive to the oral mucosa for an extended time.

Other objects and effects of the present invention will be apparent from the following description.

The inventors have conducted a series of studies about a base which is less causative of an adverse feeling on application to the oral cavity, excellent in shape retention on water absorption, and adhesive to the oral mucosa for an extended period of time. As a result, it has been found that a drug preparation applicable to the oral mucosa satisfying all these requirements is obtained by using a homogeneous mixture comprising (A) a vinyl acetate homopolymer, (B) an acrylic acid polymer, and (C) a cellulose derivative capable of being dissolved in or swollen with water and a lower alcohol (hereinafter simply referred to a cellulose derivative), thereby achieving an effective administration of a systemic drug, thus reaching the present invention.

The present invention relates to a drug preparation applicable to the oral mucosa comprising a soft adhesive film containing a systemic drug, the adhesive film comprising a homogeneous mixture comprising (A) a vinyl acetate homopolymer, (B) an acrylic acid polymer, and (C) a cellulose derivative capable of being dissolved in or swollen with water and a lower alcohol.

The present invention further relates to a drug preparation applicable to the oral mucosa having the above-described structure, wherein a soft water-insoluble support film is laminated on a side of the adhesive film.

DETAILED DESCRIPTION OF THE INVENTION

Figure 1:
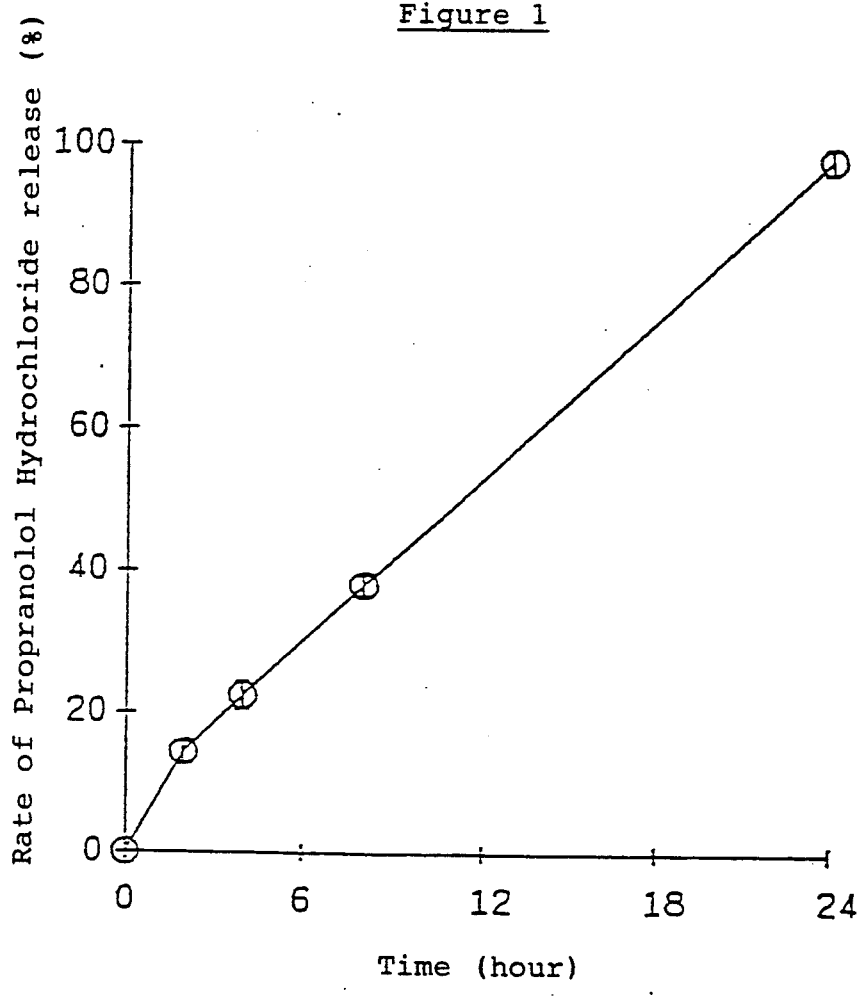
FIG. 1 illustrates the relationship of rate of Propranolol Hydrochloride release to the time.

When the drug preparation applicable to the oral mucosa according to the present invention is applied to, for example, the fore gingiva of the upper jaw, the adhesive film base absorbs saliva and a water content in the oral cavity to exhibit adhesion to the oral mucosa. The adhesiveness is retained for a long period of time because of the excellent shape retention. Since the film base is homogeneous and soft, it is tightly adhered to the oral mucosa without causing an adverse feeling during application. The terminology "homogenous" as used herein means that the vinyl acetate homopolymer, acrylic acid polymer and cellulose derivative in the mixture are homogeneously mixed under optical microscopic observation and that each of these components does not exist solely in parts.

The adhesive film of the drug preparation according to the present invention is obtained using a homogeneous mixture of a vinyl acetate homopolymer, an acrylic acid polymer, and a cellulose derivative. A two-component mixture comprising only the vinyl acetate homopolymer and the acrylic acid polymer forms a homogenous and soft film but is swollen with saliva or other water content in the oral cavity and is inferior in shape retention on application to the oral mucosa. Further, a two-component mixture comprising only the acrylic acid polymer and the cellulose derivative forms a homogeneous and soft film but does not withstand long-term use in the oral cavity because of water-solubility of these components. Furthermore, a two component mixture comprising only the vinyl acetate homopolymer and the cellulose derivative hardly forms a homogeneous and soft film.

The vinyl acetate homopolymer which can be used in the present invention is not particularly limited, and any known vinyl acetate homopolymer (as disclosed, e.g., in S.Imoto, *Plastic Zairvo Koza* (Lectures on Plastic Materials) vol. 14 Vinyl Acetate Resins, published by Nikkan Kogyo Press, Japan, on May 15, 1970) can be used as such either alone or in combination thereof The weight average molecular weight of the vinyl acetate homopolymer is preferably from 40,000 to 200,000.

Examples of the acrylic acid polymer which can be used in the present invention includes an acrylic acid homopolymer; copolymers of acrylic acid and vinyl monomers, such as acrylic esters (e.g., butyl acrylate and 2-ethylhexyl acrylate), methacrylic esters (e.g., methyl methacrylate), and vinyl acetate; and other polymers, e.g., a carboxyvinyl polymer. Among these, an acrylic acid polymer having a caboxyl group content of 20% by weight or more is preferred. These polymers may be used either alone or in combinations thereof.

The cellulose derivative which can be used in the present invention must be capable of being dissolved in or swollen with water and a lower alcohol. Examples of the cellulose derivatives include methyl cellulose, ethyl cellulose, hydroxyethyl cellulose, hydroxypropyl cellulose, and hydroxypropylmethyl cellulose. The degree of substitution of the cellulose derivative is preferably from 0.1 to 4.5, and more preferably from 1.0 to 2.5. Hydroxypropyl cellulose having a degree of substitution of from 1.3 to 2.0 is most preferred. These cellulose derivatives may be used either alone or as a mixture of two or more thereof.

A weight ratio of acrylic acid polymer (B) to cellulose derivative (C) (B/C) preferably ranges from 1/9 to 9/1. To ensure long-term adhesion to the oral mucosa, the weight ratio B/C suitably ranges from 3/7 to 6/4. A weight ratio of vinyl acetate homopolymer (A) to the sum of acrylic acid polymer (B) and cellulose derivative (C) (A/(B+C)) preferably ranges from 2/8 to 8/2. To further ensure long-term adhesion to the oral mucosa, the weight ratio B/C more preferably ranges from 4/6 to 6/4.

Thus, the working time of the preparation in the oral cavity, which partly depends on the duration of adhesion, can be appropriately controlled by varying the ratio of vinyl acetate homopolymer (A), acrylic acid polymer (B), and cellulose derivative (C).

If desired, the drug preparation of the present invention may further contain a salt or a base. That is, since the drug preparation comprising only the above-described components assumes acidity attributed to the acrylic acid polymer, it sometimes give a slight irritation to excitable parts, such as an injured part. Where such an irritation due to acidity gives rise to troubles, incorporation of a salt or base having a neutralizing effect substantially removes the irritation to the injured part.

Examples of suitable salts and bases are salts of metals and weak acids, e.g., a salt of an alkali metal (e.g., sodium and potassium) and a carboxylic acid (e.g., acetic acid, lactic acid, and citric acid); metal hydroxides, e.g., sodium hydroxide and potassium hydroxide; amines, e.g., triethanolamine and diisopropanol amine; and mixtures thereof. A salt of an alkali metal (e.g., sodium and potassium) and a carboxylic acid (e.g., acetic acid, lactic acid, and citric acid) is preferably used. The amount of the salt or base to be incorporated widely varies depending on the kind. For example, a monovalent metal salt is preferably used in an amount of from 0.03 to 0.2 equivalent to the acrylic acid polymer. Amounts less than 0.03 equivalent produce insufficient effects to reduce the irritation of an injured part. If the amount exceeds 0.2 equivalent, water resistance of the adhesive film is reduced, failing to attain sufficient adhesion to the oral mucosa.

The drug preparation applicable to the oral mucosa according to the present invention can be obtained as follows. A vinyl acetate homopolymer, an acrylic acid polymer, and a cellulose derivative are dissolved in a solvent commonly compatible to them, and a systemic drug is added to the solution to form a film-forming composition. The systemic drug in the composition may be either in a dissolved state or in a dispersed state so that the mode of addition is arbitrarily chosen. The film-forming composition is cast on a releasable liner and dried to form a film.

Examples of the solvent commonly compatible to the film-forming components includes an alcohol and a water-alcohol mixed solvent. Taking solubility of the cellulose derivative into consideration, lower alcohols, e.g., methanol and ethanol are exemplified as the alcohol. The water content in the mixed solvent is preferably not more than 30% by weight. If it exceeds 30% by weight, the vinyl acetate homopolymer tends to be hardly dissolved.

Examples of the releasable liner on which the film-forming composition is cast includes a release-treated polyethylene laminated paper, a polyethylene film, and a silicon-treated polyethylene terephthalate film.

Drying of the cast film is carried out in a high-temperature air bath using a drying oven or a drying tower, and a vacuum drier.

Thickness of the drug preparation of the present invention can be adjusted by controlling the amount of the composition cast and is preferably in the range of from 5 to 500 $\mu$m. From the standpoint of film strength and feeling on use, a thickness of from 10 to 100 μm is more preferred.

The drug preparation applicable to the oral mucosa according to the present invention basically comprises a homogeneous and soft adhesive film which is obtained from a vinyl acetate homopolymer, an acrylic acid polymer, and a cellulose derivative as described above. If desired, a water-insoluble support may be provided on the adhesive film to endow the preparation with improved shape retention on water absorption.

Examples of the water-insoluble support includes a film of a synthetic resin, e.g., polyethylene, a vinyl acetate homopolymer, an ethylene-vinyl acetate copolymer, polyvinyl chloride, and polyurethane; a metal foil, e.g., an aluminum foil and a tin foil; and a laminate film comprising cloth or paper and a synthetic resin film. From the viewpoint of safety and a feeling on use, it is preferable to use a film of a synthetic resin, e.g., polyethylene, a vinyl acetate homopolymer, and an ethylene-vinyl acetate copolymer as a support. In order to assure ease in handling and to avoid to give an adverse feeling on use, the water-insoluble support preferably has a thickness of from 10 to 100 μm.

The above-described drug preparation of a laminate type can be prepared by, for example, hot pressing the adhesive film and the water-insoluble support film. Alternatively, the laminate type drug preparation can be obtained by casting the film-forming composition on the water-insoluble support followed by drying.

The thus obtained drug preparation according to the present invention, when applied to the wet oral mucosa, absorbs water contents and is swollen with the water contents to exhibit excellent adhesion and shape retention for an extended time without causing an adverse feel, thereby liberating a systemic drug present in the preparation for a prolonged time while protecting the site. During the application, the drug can be prevented from running off due to saliva, etc., and an administration of the drug can be maintained in a stable manner.

The drug preparation of the present invention contains a systemic drug and administers it through the oral mucosa. Some drugs, when orally administered, are difficult in manifestation of efficacy commensurate with dosages because they undergo primary metabolism in the liver. Moreover, some drugs produce undesired side effects to organs, such as stomach. In order to eliminate these disadvantages associated with oral administration of drugs, preparations applicable to the skin which deliver the active ingredient by cutaneous absorption have recently called attention. However, the skin essentially functions to prevent entrance of a foreign substance into the body and does not easily absorb drugs. This is the reason why studies have been directed to the administration route through the oral mucosa which is considered to have a higher absorption of a drug than the skin. By the route through the oral mucosa, the drug preparation according to the present invention makes it possible to effectively deliver a systemic drug present in the preparation into the body.

The systemic drug which can be incorporated into the drug preparation of the invention may be either solid or liquid at room temperature, and any systemic drug which can be dissolved or dispersed in the soft adhesive film can be employed. The method for dissolving or dispersing the systemic drug in the soft adhesive film is not particularly limited. For example, the vinyl acetate homopolymer, the acrylic acid polyer and the cellulose derivative are dissolved in a solvent which is compatible to these components, and the systemic drug is separately dissolved or dispersed in the same solvent. The resulting solutions (or solution and dispersion) are mixed with each other to form a film-forming composition, and the film-forming composition is then cast on a releasable liner followed by drying so as to form the preparation.

Examples of the systemic drugs include general anesthetic agents, hypnotics, sedatives, antiepileptics, analeptics, awakening agents, anti-dizziness agents, psychoneurotropic agents, neuromuscular blocking agents, autonomic neutrotropic agents, antispasmodics, anti-Perkinson's disease, antihistaminics, stimulation therapeutics, antiallergic agents, cardiotonics, antiarrhythmics, diuretics, hypotensives, vasopressors, coronary vasopressors, peripheral vasopressors, anti-arteriosclerotic agents, agents for other circulatory organs, respiration accelerating agents, antitussive expectorants, treating agents of peptic ulcers, pituitary hormone, thyroid hormone, parathormone, androkinin, female sex hormone (i.e., vesicular ovarian follicle hormone and corpus luteum hormone), other hormones, oxytocics, agents for the urogenital system, oxygen preparations, anti-diabetic agents, other metabolic drugs, anti-tumor agents, antibiotics chemotherapeutics, and narcotics.

The amount of the systemic drug to be incorporated into the drug preparation depends on the kind of the drug and is usually selected from 0.001 to 40% by weight, preferably from 0.002 to 20% by weight, based on the adhesive film in view of the pharmacological effects and adhesion to the oral mucosa.

The drug preparation applicable to the oral mucosa according to the present invention is less causative of an adverse feeling on use, excellent in shape retention on water absorption, and adhesive to the oral mucosa for an extended period of time. Accordingly, the present invention makes it possible to maintain a stable administration of a systemic drug.

As described above, the drug preparation applicable to the oral mucosa of the present invention which comprises a soft adhesive film prepared from a homogeneous mixture of a vinyl acetate homopolymer, an acrylic acid polymer, and a specific cellulose derivative is soft, less causative of an adverse feeling in the oral cavity on use and excellent in shape retention on water absorption. Further, since the drug preparation can be adhered to the oral mucosa for a long period of time, a systemic drug present in the preparation can be stably administered for a long time. Furthermore, because of the homogeneity and softness of the film base, the drug preparation can be deformed in perfect accord with the shape of the oral mucosa simply by lightly pressing and adhered close to the mucosa.

The present invention is now illustrated in greater detail by way of the following Examples, but it should be understood that the present invention is not deemed to be limited thereto. In these examples, all the parts, percents and ratios are by weight unless otherwise specified.

Prior to conducting the examples, an agar gel as a substitution for the oral mucosa was prepared as follows.

Preparation of Agar Gel

Distilled water was added to 2 g of an agar powder (Japanese Pharmacopeia) to make 100 g, and the mixture was boiled to completely dissolve the agar. The solution was poured into a dish and allowed to cool to prepare an agar gel.

EXAMPLE 1

Five parts of a vinyl acetate homopolymer (weight average molecular weight: 129,000), 2 parts of a carboxyvinyl polymer (carboxyl group content: 58–63% by weight) (as the acrylic acid polymer), 3 parts of hydroxypropylmethyl cellulose (degree of substitution: 1.86–1.90) (as the cellulose derivative), 0.2 part of diisopropanolamine (as the base for neutralizing the acrylic acid polymer), and 2 parts of Propranolol Hydrochloride (as the systemic drug) were added to 90 parts of a 2/8 water-methanol mixture as a common solvent to prepare a film-forming composition containing the systemic drug. The composition was cast on a silicon-release paper, dried, and stripped off to obtain a 30 μm thick adhesive film. A 20 μm thick soft alumina foil as a water-insoluble support was hot-pressed on the resulting adhesive film to obtain a drug preparation applicable to the oral mucosa.

EXAMPLE 2

Five parts of a vinyl acetate homopolymer (weight average molecular weight: 129,000), 2 parts of a carboxyvinyl polymer (carboxyl group content: 58–63% by weight) (as the acrylic acid polymer), 3 parts of hydroxypropylmethyl cellulose (degree of substitution: 1.86–1.90) (as the cellulose derivative), and 0.5 parts of Sodium Indometacin (as the systemic drug) were added to 90 parts of a 1/9 water-methanol mixture as a common solvent to prepare a film-forming composition. The composition was cast on a silicon-release paper, dried, and stripped off to obtain a 60 μm thick adhesive film. A 20 μm thick soft vinyl acetate film as a water-insoluble support was hot-pressed on the resulting adhesive film to obtain a preparation applicable to the oral mucosa.

Evaluation

Specimens having a size of 1 cm×2 cm was cut out of each of the drug preparations obtained in Examples 1 and 2 and adhered to the surface of the above-prepared agar gel. After a prescribed period of time, the specimen was peeled off the agar gel and extracted from 50 ml of methanol. The drug in the extract was determined by high performance liquid chromatography. The resulting data of Examples 1 and 2 were plotted in FIGS. 1 and 2, respectively, with rate of drug release as ordinate and time as abscissa.

Figure 2:
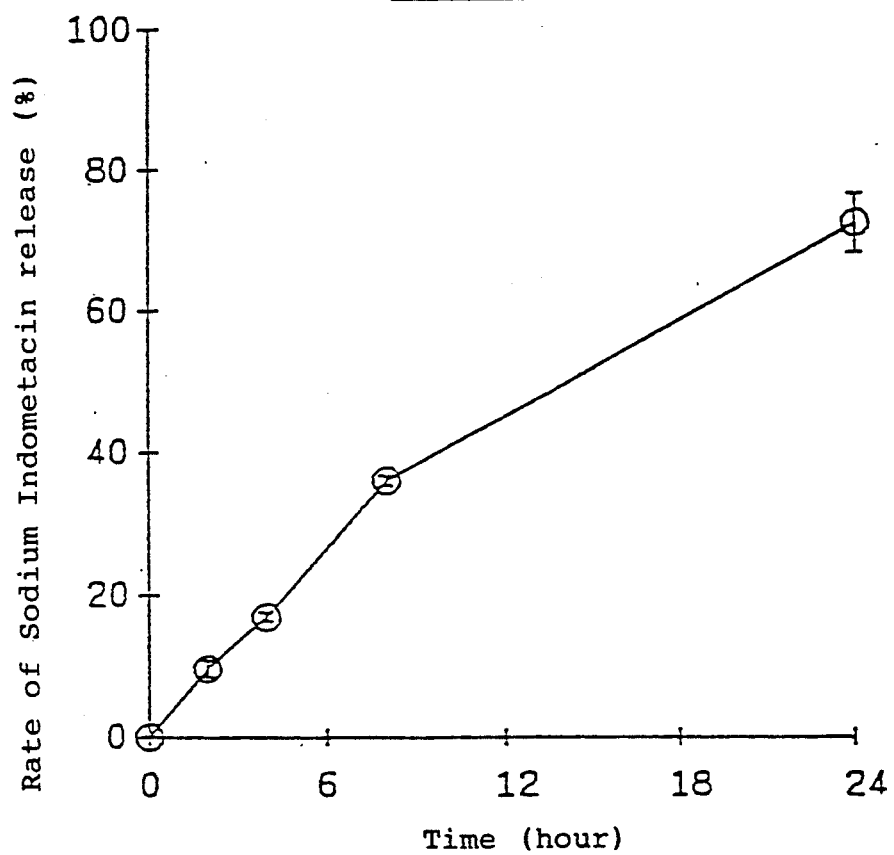
FIG. 2 illustrates the relationship of rate of Sodium Indometacin release to the time.

It can be seen from FIGS. 1 and 2 that the drug preparation according to the present invention keeps adhered to the agar gel, a substitution for the oral mucosa, for a long time so that the active ingredient in the preparation is stably and steadily released with time.

Further, the specimens were adhered to the oral mucosa of panel members to conduct organoleptic test of a feeling. As a result, the specimens were judged to have little adverse feeling.

While the invention has been described in detail and with reference to specific embodiments thereof, it will be apparent to one skilled in the art that various changes and modifications can be made therein without departing from the spirit and scope thereof.

What is claimed is:

1. A drug preparation applicable to the oral mucosa, comprising a soft adhesive film containing a systemic drug, said adhesive film comprising a homogeneous mixture comprising a vinyl acetate homopolymer, an acrylic acid polymer, and a cellulose derivative capable of being dissolved in or swollen with water and a lower alcohol, wherein said cellulose derivatie is selected from the group consisting of methyl cellulose, ethyl cellulose, hydroxyethyl cellulose, hydroxy-propyl cellulose, and hydroxypropylmethyl cellulose.

2. A drug preparation as claimed in claim 1, wherein said acrylic acid polymer and cellulose derivative are present at a weight ratio of from 1/9 to 9.1.

3. A drug preparation as claimed in claim 2, wherein said acrylic acid polymer and cellulose derivative are present at a weight ration of from 3.7 to 6.4.

4. A drug preparation as claimed in claim 1, wherein a weight ratio of said vinyl acetate homopolymer to the sum of said acrylic acid polymer and cellulose derivative is from 2/8 to 8.2.

5. A drug preparation as claimed in claim 4, wherein said acrylic acid polymer and cellulose derivative are present at a weight ratio of from 4/6 to 6/4.

6. A drug preparation as claimed in claim 1, wherein said adhesive film further contains a salt or base neutralizing the acrylic acid polymer.

7. A drug preparation as claimed in claim 6, wherein said salt or base is present in an amount of from 0.03 to 0.2 equivalent to the acrylic acid polymer.

8. A drug preparation as claimed in claim 1, wherein said adhesive film has a thickness of from 5 to 500 μm.

9. A drug preparation as claimed in claim 2, wherein said preparation further comprises a water-insoluble soft film support laminated on said adhesive film.

10. A drug preparation as claimed in claim 9, wherein said support has a thickness of from 10 to 100 μm.

11. A drug preparation as claimed in claim 9, wherein said support is a polyethylene film, a vinyl acetate homopolymer film or an ethylene-vinyl acetate copolymer film.

12. A drug preparation as claimed in claim 1, wherein said lower alcohol is selected from the group consisting of methanol and ethanol.

* * * * *